United States Patent [19]

Walker

[11] 4,088,447

[45] May 9, 1978

[54] ADIABATIC CALORIMETER APPARATUS AND METHOD FOR MEASURING THE ENERGY CHANGE IN A CHEMICAL REACTION

[75] Inventor: Lynn Charles Walker, Midland, Mich.

[73] Assignee: The Dow Chemical Company, Midland, Mich.

[21] Appl. No.: 763,261

[22] Filed: Jan. 27, 1977

Related U.S. Application Data

[63] Continuation-in-part of Ser. No. 624,613, Oct. 22, 1975, abandoned.

[51] Int. Cl.$^2$ .................... G01K 17/00; G01N 25/20
[52] U.S. Cl. ............................. 23/230 R; 23/253 R; 73/190 R
[58] Field of Search .......... 23/230 R, 253 R, 259 US; 73/190 R

[56] References Cited

U.S. PATENT DOCUMENTS

| | | | |
|---|---|---|---|
| 2,658,819 | 11/1953 | Formwalt | 23/253 R |
| 2,982,132 | 5/1961 | Mendlowitz | 73/190 R |
| 3,160,477 | 12/1964 | Wasilewski | 23/253 R |
| 3,365,944 | 1/1968 | Hoagland et al. | 73/190 R |
| 3,718,437 | 2/1973 | Paloniemi | 23/253 R |
| 3,765,237 | 10/1973 | Blackmer et al. | 73/190 R |
| 3,881,872 | 5/1975 | Naono | 23/253 R |
| 3,915,636 | 10/1975 | Ford, Jr. et al. | 23/253 R X |

*Primary Examiner*—Joseph Scovronek
*Attorney, Agent, or Firm*—V. Dean Clausen

[57] ABSTRACT

A novel adiabatic reaction calorimeter useful for mesuring the energy change in a chemical reaction is disclosed. In a specific application, the calorimeter is used to measure the heat energy derived in a chemical reaction. The device includes a reaction vessel which is thermally isolated in the geometric center of a sealed spherical chamber. The chamber, which is filled with a gas atmosphere, is defined within a box structure fabricated of a ceramic foam or plastic foam. An auxiliary vessel is positioned in the chamber adjacent to the reaction vessel and is connected to the reaction vessel by a transfer conduit.

In a typical operation, prior to initiating the reaction, one reactant is contained in the reaction vessel and another reactant in the auxiliary vessel. The vessels and the gas atmosphere are heated to a predetermined temperature by electrical power units, with regulation by a temperature control unit. When a desired temperature is reached the reactant in the auxiliary vessel is released into the reaction vessel to initiate the reaction. During the reaction the reaction mixture is continuously stirred in the reaction vessel and the gas atmosphere is circulated in a symmetrical pattern within the chamber. The actual change in temperature which the reaction vessel undergoes during the reaction, together with an electrical calibration of the vessel enables measurement of the energy change.

11 Claims, 2 Drawing Figures

ADIABATIC CALORIMETER APPARATUS AND METHOD FOR MEASURING THE ENERGY CHANGE IN A CHEMICAL REACTION

CROSS REFERENCE TO RELATED APPLICATION

This application is a continuation-in-part of U.S. Application Ser. No. 624,613, filed Oct. 22, 1975, now abandoned.

BACKGROUND OF THE INVENTION

Broadly, the invention relates to an apparatus and method for measuring the energy change in a chemical reaction. More specifically, the invention is directed to an adiabatic reaction calorimeter for measuring heat energy, and a method of use.

The term calorimetry can be generally defined as measurement of energy in the form of heat. The science of calorimetry is widely used in the chemical industry to measure the quantity of heat which is liberated or absorbed in various processes, such as chemical reactions, changes of state, formation of solutions, and in determining heat capacities of substances. To cite a specific example, the chemical engineer usually needs to have a knowledge of the heat of reaction involved in a chemical process in order to properly calculate heat balances.

Over a period of years many different types of calorimeters have been developed for measuring heat energy. One of the conventional devices now in use is referred to as an adiabatic reaction calorimeter. In an adiabatic calorimeter the objective is to minimize heat transfer between the calorimeter and the surrounding structure and atmosphere.

A typical adiabatic calorimeter is used by the National Bureau of Standards, at Washington, D.C. This device is an adaptation of a heat capacity calorimeter, which employs a vacuum chamber and a radiation control shield. In this device a bomb vessel is suspended in the center of an evacuated cubical steel box designed to withstand a high vacuum. The bomb vessel is supported inside a cylindrical heat radiation shield, which has a heating (resistance) wire secured to the inner surfaces of the shield.

During a chemical reaction the temperature of the radiation shield is matched to the temperature of the bomb vessel by an electronic control system, which includes differential thermocouples on the bomb vessel and the shield. The purpose of the radiation shield and control system is to minimize heat transfer from the bomb vessel to the surrounding vacuum environment. A platinum resistance thermometer on the bomb vessel measures temperature change, and a calibration heater is also attached to the bomb vessel. The bomb vessel and radiation shield are attached to a rotatable shaft, which rotates the entire unit in opposite directions, to mix the contents of the bomb vessel during the reaction.

A typical experiment which can be carried out in this device is to determine the heat of combustion of an organic compound, such as phthalic acid. In the procedure the bomb vessel is charged with oxygen, at an operating pressure of about 500 p.s.i. The bomb vessel is provided with a resistance thermometer, calibration heater and electrodes for igniting a sample of the organic compound. The entire chamber (box) is evacuated with a high vacuum pump. After evacuation the temperature of the bomb vessel is adjusted and the radiation shield control is turned on. When the thermal (temperature) drift becomes constant, the organic sample is electrically ignited to initiate the combustion reaction.

As the temperature of the bomb vessel increases, the automatic shield control brings the shield up to the same temperature as the bomb. This is done to minimize heat loss, as explained above. Shortly after the sample is ignited, the bomb vessel is rotated, to wash down the walls of the vessel to insure a homogeneous solution. When the thermal drift again becomes constant, the reaction is complete, and the unit is disassembled. The system can be calibrated by adding a known quantity of electrical energy to the bomb vessel and by observing the temperature change, or by burning a compound, such as benzoic acid, which is designated as a standard by the National Bureau.

The adiabatic calorimeter device described above has several disadvantages. A major problem is that the device has a limited temperature range, since the steel box enclosure is not insulated. Another problem is that the device does not include separate vessels for keeping reactants separated prior to a reaction. This is an obvious drawback, since it is essential in many heat of reaction studies to keep the reactants separated until it is desired to observe the temperature change. Another problem is the complex construction of the device, which requires that the entire bomb and radiation shield assembly be rotated at the same time. This part of the device is not only a complex structure, but it is impractical for measuring energy change in a slow reaction.

SUMMARY OF THE INVENTION

The invention concerns an adiabatic calorimeter apparatus, and method of use, for measuring the energy change in a chemical reaction. In a preferred embodiment, the apparatus includes a reaction chamber defined by a cavity positioned within an insulated box structure. The cavity is filled with a gas atmosphere, usually room air. Positioned inside the cavity are two vessels; one is an auxiliary vessel, the other is referred to as a reaction vessel (bomb vessel).

The auxiliary vessel is connected into a source of gas under pressure. A transfer conduit connects the auxiliary vessel to the reaction vessel. Prior to initiating the chemical reaction, one reactant is contained in the auxiliary vessel and another reactant in the reaction vessel. A heater means and a temperature measuring means are positioned inside the reaction vessel. The heater is connected into an electrical power supply and the temperature measuring means is connected into a temperature recording unit.

The calorimeter apparatus includes two differential temperature sensing systems. In the first system several temperature sensors are attached to the outside of the reaction vessel. These temperature sensors are connected into opposing temperature sensors attached to an inner wall surface of the reaction chamber. Both sets of temperature sensors are connected into a temperature control unit. In turn, the control unit is connected into a power supply and a set of heaters; the heaters being attached to the wall surface of the reaction chamber. The function of the first system is to detect any temperature difference between the reaction vessel and the gas atmosphere. If a temperature difference occurs, the control unit takes corrective action to maintain the temperature of the reaction vessel and the gas atmosphere at equilibrium.

A second differential temperature sensing system provides a means for keeping the temperature of the auxiliary vessel and the reaction vessel at the same level. In this system, one or more temperature sensors are attached to the outside of the auxiliary vessel. These sensors are, in turn, connected into opposing temperature sensors attached to the outside of the reaction vessel. A sleeve heater is also attached to the auxiliary vessel. The heater and both sets of temperature sensors are connected into a temperature control unit similar to the unit used in the first system. This control unit is also connected into a separate power supply.

In a typical operation for measuring an energy change, the auxiliary vessel, the reaction vessel, and the gas atmosphere are heated to a predetermined initial temperature. When the desired temperature is reached the chemical reactant in the auxiliary vessel is transferred into the reaction vessel by applying the gas under pressure to the auxiliary vessel. This initiates a chemical reaction in the reaction vessel. During the reaction the reactants are continuously stirred by a stirring means in the reaction vessel. Also, a circulating means in the reaction chamber provides a means for continuously circulating the gas atmosphere in the chamber. As the reaction proceeds the temperature of the reaction vessel will change from the temperature observed at the start of the reaction. This temperature change is continuously measured by the temperature measuring means and is recorded by the temperature recorder unit.

DESCRIPTION OF A PREFERRED EMBODIMENT

Figure 1:
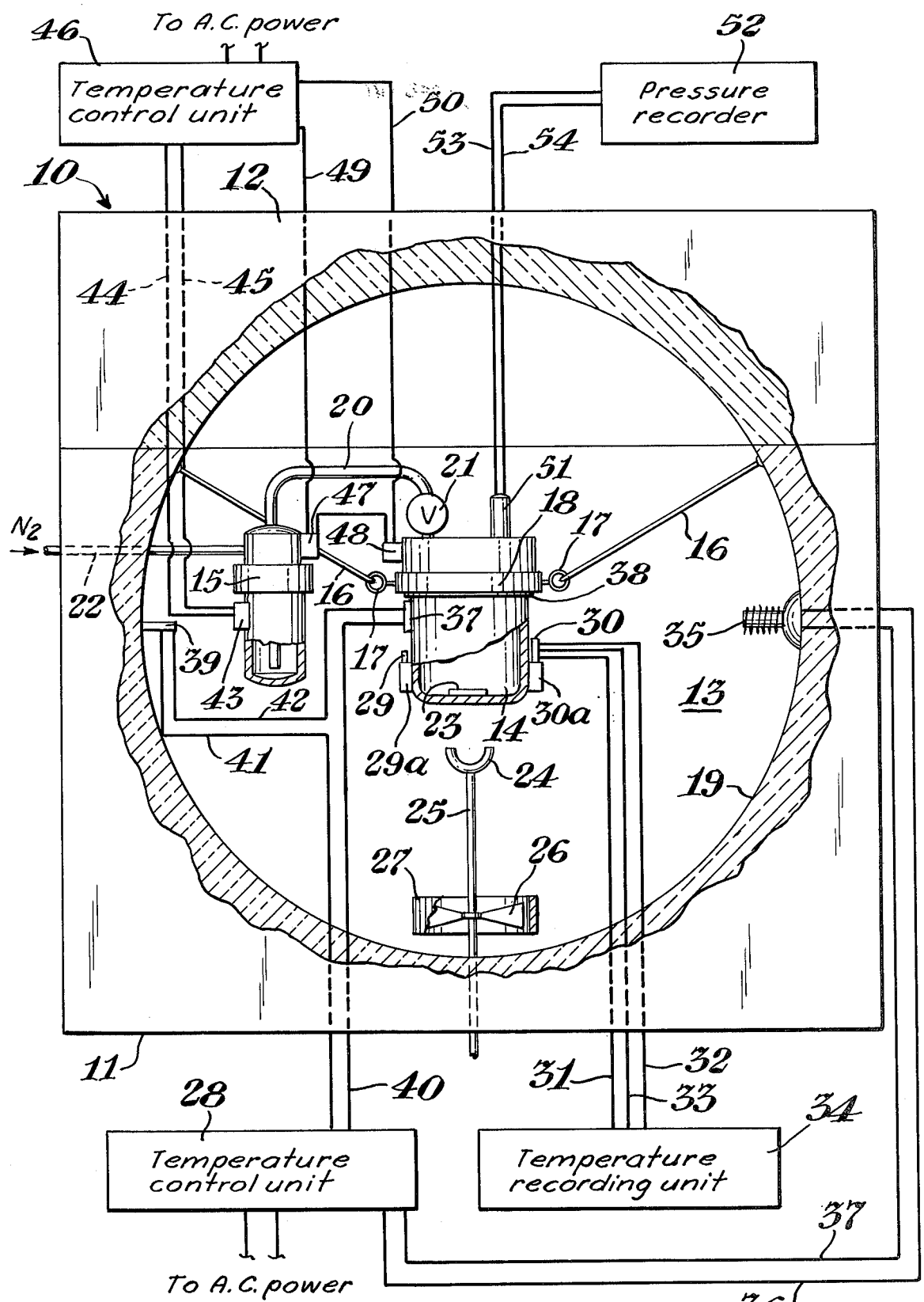
FIG. 1 is a view partly in section, and partly schematic of one embodiment of a calorimeter apparatus according to this invention.

In the drawing, the apparatus illustrated in FIG. 1 is referred to as an adiabatic reaction calorimeter. Basically, the apparatus is made up of a box structure, indicated generally by numeral 10. The box 10 includes a base 11 and a removable lid 12. When the box is in closed position, as shown in FIG. 1, the inside of the box defines a spherical cavity 13, which provides a reaction chamber.

The box structure should be fabricated of materials which have good insulating properties, such as synthetic resinous or inorganic materials. Typical of synthetic resinous materials which may be used are foam materials, such as a polystyrene foam sold under the name Styrofoam ®. In practice, the reaction chamber 13 can operate at temperatures in the range of −100° C. to +1000° C. At temperatures from −10° C. to +1000° C., the chamber should be fabricated of inorganic materials, such as ceramic foam. For a temperature range of from −100° C. to +100° C., the chamber can be constructed of synthetic resinous foam materials. Other suitable inorganic materials which may be used to construct the box structure are ceramic brick, glass brick, or refractory materials.

A spherical configuration is preferred for the chamber 13. In the practice of this invention, the chamber 13 is filled with a gaseous atmosphere, such as air or an inert gas. When the operating temperature in chamber 13 is above about 0° C., room air provides a suitable atmosphere. At operating temperatures below about 0° C., an atmosphere such as nitrogen, or carbon dioxide, should be used. The reason for this is that at the lower temperatures the water vapor present in room air will condense, and may cause corrosion of the metal parts in the chamber.

A reaction vessel 14 and auxiliary vessel 15 are positioned within the gaseous atmosphere of chamber 13. To achieve good thermal isolation, it is preferred to suspend the reaction vessel 14 at the geometric center of the cavity. A suitable reaction vessel may be fabricated of stainless steel, and the vessel should include an inner platinum lining. Reaction vessel 14 is suspended in chamber 13 by small diameter wires or cords which have low thermal conductivity. Suitable wire materials are stainless steel, or a polyester fiber cord, such as Dacron ®.

In the embodiment illustrated herein, the reaction vessel 14 is suspended in chamber 13 by stainless steel wires 16. One end of each wire 16 is fastened to an eye bolt 17, which is secured to a flange 18 on the reaction vessel 14. The other end of each wire is fastened into a wall surface 19, which is defined at the periphery of chamber 13. A transfer conduit 20 connects the auxiliary vessel 14 with the reaction vessel 15. A small valve 21 is installed in conduit 20, preferably at a point where the conduit 20 enters the reaction vessel 14.

Prior to initiating a chemical reaction in reaction vessel 14, the reactants are separated. One of the reactants is contained in reaction vessel 14 and the other in auxiliary vessel 15. To start the reaction, a gas under pressure, such as nitrogen, is passed into auxiliary vessel 15 through a gas supply line 22, which is connected into the top of the auxiliary vessel 15. The pressurized gas released into auxiliary vessel 15 forces the reactant out of vessel 15, through the transfer conduit 20, and into the reaction vessel 14.

During the reaction, the reaction mixture in reaction vessel 14 is continuously stirred by a resin-coated metal stir bar 23, which is loosely positioned in the reaction vessel 14. The stir bar 23 is rotated by a magnet 24, which is connected to the upper end of a rotatable shaft 25. The shaft 25 extends through a bottom wall of the base 11 into the chamber 13. This shaft is driven by a motor (not shown), which is positioned outside the box structure 10.

In addition to continuously stirring the reaction mixture in reaction vessel 14, the gas atmosphere in chamber 13 is continuously circulated, in a symmetrical pattern, around the reaction vessel 14. Circulation of the gas atmosphere minimizes heat transfer, either into the reaction vessel or away from it. The circulating means is provided by a fan blade 26, which is mounted on the shaft 25 near the bottom of the reaction chamber 13. Also, the fan blade 26 is enclosed by a circular skirt member 27.

The symmetrical pattern of the circulating air in chamber 13 is caused by the combined effect of fan blade 26 and the skirt 27. More specifically, a venturi effect is created in which the atmosphere is continuously forced to flow along the chamber wall, thus combining at the top or bottom of the chamber and then flowing through the center of the chamber to circulate over the reaction vessel in particular. The flow pattern is such as to provide complete circulation of the atmosphere around both the reaction vessel 14 and the auxiliary vessel 15.

A temperature control unit 28 is provided for the calorimeter. This control unit is a commercially available component which includes a current-adjust-type deviation control module. The control module employs proportional band, derivative and integral control modes. The control unit also includes a high gain, solid state, stabilizing amplifier, which drives the control module, and a solid state, phase-firing transistor switch.

Means for heating the reaction vessel 14 is provided by a heater element 29, which is mounted on or embedded in a metal body, such as a copper disc 29a. In turn, the disc is attached to one side of reaction vessel 14 near the bottom of the vessel. The heater 29 may be a bifilar wound resistance element, which is connected to a constant current power supply (not shown). Components of the power supply generally include a digital voltmeter and a timer device. Means for measuring the temperature of the reaction vessel 14 is provided by a platinum resistance thermometer 30. The thermometer is mounted on or embedded in a metal body, such as a copper disc 30a. In turn, the disc is attached to bomb vessel 14, preferably on the opposite side of the vessel from the heater element 29.

The thermometer 30 is connected by electrical leads 31, 32, and 33 to a temperature recording unit 34. Preferably, unit 34 is a recording Müller bridge. The gas atmosphere in reaction chamber 13 is heated by a number of resistance heaters 35. These heaters are mounted at equally spaced points on the inner wall surface 19 of the spherical chamber 13. Any number of heaters may be used to give the desired heating action. In practice, it is preferred to use four heaters. Only one of the heaters 35 is illustrated in the drawing. As shown, heater 35 is connected to the temperature control unit 28 by electrical leads 36 and 37.

In the calorimeter of this invention there are two systems for sensing reaction heat generated in the reaction vessel 14, such as in an exothermic chemical reaction, or for sensing heat absorbed by the bomb, such as in an endothermic chemical reaction. One system is provided by the platinum resistance thermometer 30, which is connected to the temperature recording unit 34. The other system is provided by a number of thermocouples 37, which are attached to a metal band 38 on the bomb vessel 14. The band 38 may be made of copper or any other metal having good thermal conductivity. In the drawing only one thermocouple 37 is shown. In practice, an array of four thermocouples is preferred.

The thermocouples 37 on the reaction vessel 14 are opposed by four identical thermocouples, which are mounted at equally spaced points on the inner wall surface 19 of chamber 13. Only one of the thermocouples on wall surface 19, which is indicated by numeral 39, is indicated in the drawing. The thermocouples 37 and 39 are preferably made of a nickel-chromium (Chromel-P) and copper-nickel (Constantan) alloy composition. The opposing thermocouples 37 and 39 are connected in a series relationship to the temperature control unit 28 by electrical leads 40, 41 and 42.

The array of opposing thermocouples enables the temperature control unit 28 to immediately detect a temperature differential between the reaction vessel 14 and the gas atmosphere surrounding the reaction vessel. If the control unit 28 senses a temperature differential, it will automatically take corrective action. The action taken is to modulate the flow of electric current through the resistance heaters 35, to adjust the temperature of the gas atmosphere so that is coincides with the temperature of the bomb vessel 14.

A small sleeve heater 43 is mounted on the auxiliary vessel 15. Heater 43 is connected by electrical leads 44 and 45 to a temperature control unit 46 (identical to temperature control unit 28). A thermocouple 47 is also mounted on auxiliary vessel 15, and a similar opposing thermocouple 48 is mounted on the reaction vessel 14. These thermocouples are connected together, in series, by an electrical lead (not numbered). Each of the opposing thermocouples is also connected into the temperature control unit 46, by electrical leads 49 and 50.

The opposing thermocouples 47 and 48 enable the temperature control unit 46 to sense any temperature differential between the reaction vessel 14 and the auxiliary vessel 15. If a temperature difference is detected the control 46 supplies more power to heater 43 to bring the temperature of the auxiliary vessel up to the same temperature as the reaction vessel. As shown in the drawing, only one thermocouple 47 is mounted on the auxiliary vessel and one thermocouple 48 on the reaction vessel. In the practice of this invention, any number of thermocouples may be used on each vessel to obtain the desired temperature control.

Frequently, there may be a need to measure the pressure developed during a chemical reaction, in addition to measuring the heat energy developed in the reaction. For example, a knowledge of the pressure generated during a chemical reaction may be essential in designing a reactor vessel which is safe to operate. Pressure measurements are obtained from a pressure transducer 51, which is mounted in the cover of bomb vessel 14. The transducer is connected to a recorder 52 by electrical leads 53 and 54. To obtain the pressure readings, the transducer 51 transmits an electrical signal to the recorder 52, which gives the readout in pressure units.

Figure 2:
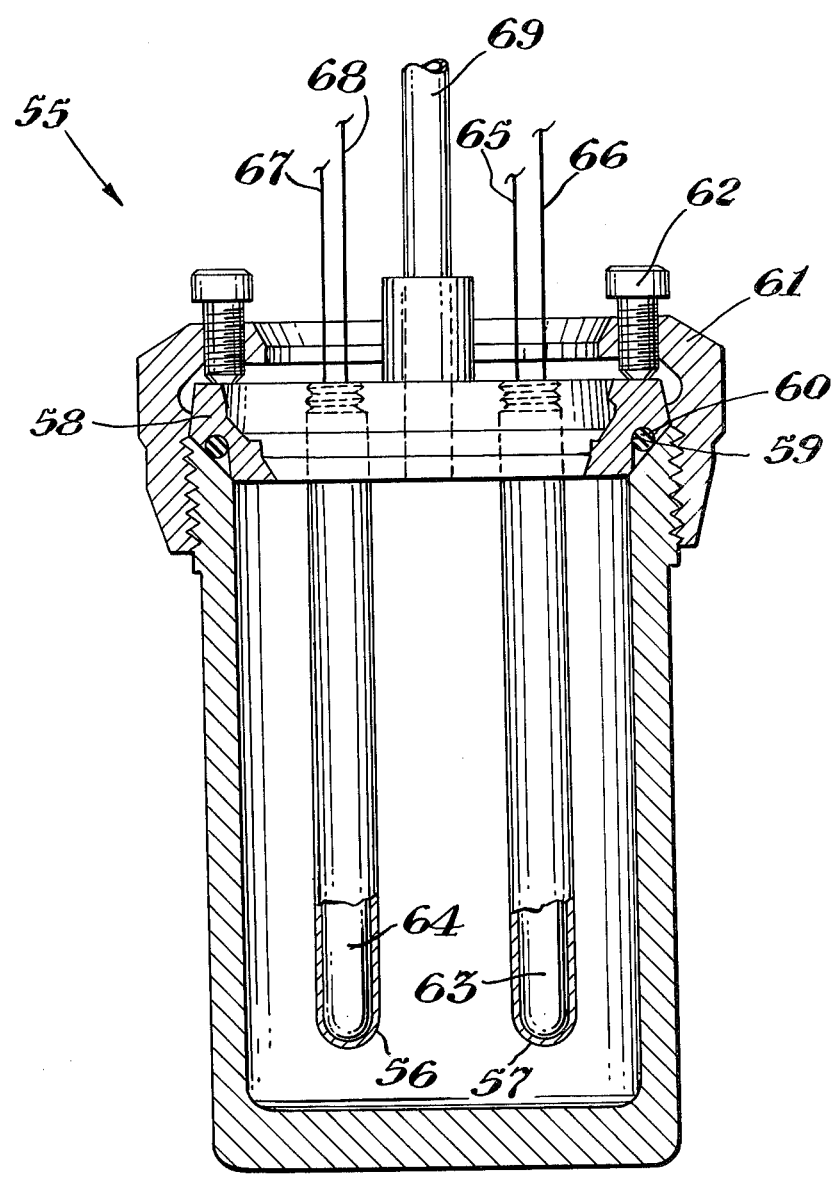
FIG. 2 is a detail view of an alternative embodiment of a reaction vessel, which can be used in the apparatus illustrated in FIG. 1.

The illustration of FIG. 2 is a detail view of a second embodiment of a reaction vessel which may be used in the calorimeter apparatus shown in FIG. 1. In this reaction vessel, indicated generally by numeral 55, the reaction mixture is heated in a more direct manner than in the reaction vessel 14 shown in FIG. 1. Also, in the vessel 55, the temperature change which takes place in the reaction mixture is measured in a more direct manner than is possible in the reaction vessel shown in FIG. 1. This is accomplished by placing the heater for the reaction vessel and the temperature measuring means in well members which are placed inside the reaction vessel.

Referring to FIG. 2, a heater well 56 and a thermometer well 57 are shown in position inside the reaction vessel 55. A lid 58 is secured to the top of the reaction vessel 55. The upper end of each well 56 and 57, which is open, extends through the lid 58 and is sealed to the lid. The lower end of each well extends down into vessel 55 to a point near the bottom of the vessel. Each well is closed at the lower end to prevent chemical reactants from entering the well. The well members may be fabricated of stainless steel or other corrosion-resistant and heat-resistant metals.

The outer edge of lid 58 defines a beveled surface with a groove 59 therein. An O-ring 60 fits into the groove 59. When lid 58 is in position on the body of vessel 55 the beveled surface of lid 58 fits against a corresponding beveled surface on the vessel body. The O-ring 60 thus insures a tight seal between the lid and the vessel.

A screw cap 61 engages a threaded portion at the outer edge of the open upper end of vessel 55. Several cap screws 62, which are threaded into screw cap 61, engage the upper surface of lid 58. The screws 62 thus force the lid 58 downwardly against the beveled surface on the body of vessel 55. A thermometer 63 fits inside the well 57. An electric thermometer, such as a platinum resistance thermometer, or a digital thermometer, is preferred.

Means for heating the reactants in vessel 55 is provided by a heater element 64, which fits inside the heater well 56. The heater used in the present apparatus is a bifilar wound resistance element. The thermometer 63 is connected into the recording unit 34 (shown in FIG. 1) by electrical leads 65 and 66. Electrical leads 67 and 68 connect the heater element 64 into a constant current power supply (not shown). Thermometer 63 and heater 64 are thus connected to the recorder unit and power supply using the same arrangement employed in connecting the thermometer 30 and heater 29 (FIG. 1) to the recorder and power supply.

The dimensions of the well members 56 and 57 are such that thermometer 63 and heater 64 are interchangeable, that is, each device will fit into either well. Means for transferring a chemical reactant from auxiliary vessel 15 (shown in FIG. 1) into the reaction vessel 55 is provided by a transfer conduit 69. Conduit 69 is connected into vessel 55 in an arrangement similar to that used for connecting conduit 20 into vessel 14 (FIG. 1). A pressure transducer (not shown) is also installed on the reaction vessel 55 in situations where it is desired to obtain pressure measurements. The same type of transducer 51 and recorder 52 components used in the embodiment of FIG. 1 are preferred.

Referring again to the embodiment illustrated in FIG. 1, there are two systems for sensing temperature differential, as described earlier. In one system any temperature differential between the reaction vessel 14 and the gas atmosphere (in chamber 13) is corrected by the temperature control unit 28. In the other system any temperature differential between the reaction vessel 14 and auxiliary vessel 15 is corrected by the temperature control unit 46. These temperature sensing systems are also used in conjunction with the reaction vessel 55 (FIG. 2) and the operation of each system is the same as described earlier.

In another embodiment of this invention, which is not illustrated, the calorimeter apparatus includes several auxiliary vessels. For example, several auxiliary vessels are required to conduct multistep reactions, or consecutive reactions, in which the reactants must be kept separated prior to initiating the reaction. Each auxiliary vessel, which can be a different size, is positioned in the reaction chamber and is connected by a transfer conduit to the reaction vessel. A specific example would be a situation in which there is a need to catalyze a polymerization reaction. The procedure would involve adding a diluent to the reaction vessel, after catalysis, to dissolve the polymer and thus insure uniform physical and chemical properties.

To carry out this multi-step reaction the calorimeter apparatus would include one auxiliary vessel containing a small amount of a catalyst. This auxiliary vessel would be connected to the reaction vessel by a transfer conduit. A remotely-operated control valve would be installed in the transfer conduit. The apparatus would also include a larger auxiliary vessel, for containing a diluent. The larger vessel would also be connected into the reaction vessel by a transfer conduit, in which a remotely-operated valve was installed. Operating the valves according to a certain sequence would allow the catalyst to enter the reaction vessel first, followed by the diluent. The heat effect which could be observed would represent initiation of the polymerization reaction, plus the heat of solution of the reactants in the diluent.

The following example is given to illustrate the invention:

EXAMPLE

The objective in this example was to determine the heat of reaction required to sulfonate a styrene polymer, with $H_2SO_4$, to obtain a sulfonated polymer product. This reaction was carried out in the reaction vessel 14, as illustrated in FIG. 1. In actual practice, the reaction could also be carried out in the reaction vessel 55, as shown in FIG. 2. The procedure for conducting the reaction in vessel 55, and the energy measurement data obtained, would be the same as described in this example. The operating conditions simulate actual process conditions encountered in a chemical plant.

The polymeric material was in the form of macroporous, semi-transparent, spheriod beads, with an average diameter of about 0.2 mm. The acid reactant was in the form of an aqueous solution, 96.8% concentration. An excess of the acid reactant was used to drive the reaction to completion, the specific mole ratio being 6 moles $H_2SO_4$/1 mole repeating polymer unit. To begin the procedure, the liquid reactant, 112.4 grams $H_2SO_4$, was placed in auxiliary vessel 15 and the vessel was sealed. The solid reactant, which was 21.44 grams of the styrene polymer, was placed in the reaction vessel 14 and the vessel was sealed. The closed vessels 14 and 15, with reactants therein, were placed in chamber 13 and lid 12 was closed. The atmosphere in chamber 13 was thus room air at room temperature.

From previous studies, it was determined that a suitable temperature range for initiating the reaction would be between about 110° C and 140° C. To prepare the calorimeter, the temperature in reaction chamber 13 was gradually raised from room temperature to 138.64° C. At this point the temperature of the reaction vessel 14, the auxiliary vessel 15, and the air in chamber 13 were at equilibrium. When the equilibrium temperature was reached, as sensed by the resistance thermometer 30, a plot line being traced on a strip chart (not shown) in the recording unit 34 changed from a sloping line to a linear line.

The linear trace provides a base line reference for initiating the reaction. To start the reaction, an inert gas, such as nitrogen, at a pressure of about 5 psig, was applied to auxiliary vessel 15. Simultaneously, the valve 21 in conduit 20 was opened, to release the gas pressure in auxiliary vessel 15 and thus force the acid reactant from vessel 15 into the reaction vessel 14 through the transfer conduit 20. In a preferred method, the reaction vessel is evacuated before initiating the reaction. This is done to facilitate a complete transfer of the acid reactant from auxiliary vessel 15 into the reaction vessel 14 when valve 21 is open. Immediately following transfer of the acid reactant into vessel 14, the recording unit 34 starting tracing an upwardly sloping plot line on the chart. The upwardly sloping line was a direct indication that the sulfonation reaction taking place in vessel 14 was an exothermic reaction.

During the course of the reaction the acid-polymer slurry in bomb vessel 14 was continuously stirred by the rotating stir bar 23. In addition, the air in chamber 13 was continuously circulated by the rotating fan blade 26. After about 50 minutes, the plot line on the chart in recording unit 34 began to change from an upward slope to a linear trace. The linear trace thus indicated a completion of the reaction. The temperature reading from the chart in recording unit 34, at the point of this second linear trace, was 143.47° C. The total temperature rise during the reaction, therefore, was 4.83° C.

As a routine procedure, the temperature of the air in chamber 13 was held at the high point (143.47° C) for about 30 to 45 minutes. The reason for this delay period is to enable accurate measurement of the heat of reaction in the event a second reaction takes place. To explain further, it is desirable not to allow the temperature of the air to cool below the temperature of the reaction vessel 14 immediately after completion of the first reaction. If this happens there will be significant heat transfer away from the reaction vessel, so that an adiabatic environment is not maintained at the time the second reaction takes place.

Following the delay period, the next step was to calibrate the reaction vessel 14. The calibration step was necessary to calculate the energy equivalent (heat capacity) of the reaction products and the reaction vessel. Once the energy equivalent is known, this figure is related to the actual temperature rise during the reaction, and the actual energy change can be calculated. It is convenient to calibrate the reaction vessel and the contents of the vessel electrically, since electrical input to the reaction vessel and heat input from a chemical reaction will result in the same energy change.

In the calibration procedure the first step was to bring the system down to the starting temperature of 138.64° C. This was done by shutting off the temperature control unit 28 to allow the system to cool to the starting temperature. At the starting temperature point, a constant electric current was metered into heater 29 from its own power supply. When the temperature of the bomb vessel reached 144.48° C., the current to the heater 29 was shut off. The time required for the reaction vessel 14 to undergo the differential temperature change of 5.84° C. was measured by a timer in the power supply circuit. The current and the voltage required to heat the bomb through this temperature change was measured by the potentiometer and the voltmeter in the power supply. The current required was 0.50383 amperes, the voltage was 10.3861 volts, and the time was 2,280 seconds (38 minutes).

Following the calibration step the current to heater 29 was shut off, and the reaction vessel was allowed to cool to room temperature. The reaction vessel was removed from the reaction chamber 13, placed under a hood, and opened for sampling. The sample was analyzed to determine the percent conversion of the polymer to the sulfonate product.

The conversion was calculated as follows:
21.44 = grams of styrene polymer starting material
112.6 = grams/repeating polymer unit
(21.44/112.6) = 0.1904 = gram moles of polymer
0.1860 = gram moles of sulfonate produced in the reaction
(0.1860/0.1904) = 97.7 = percent conversion of polymer to sulfonate The first step in measuring the energy equivalent of the reaction vessel was to calculate electrical heat input. An equation based on Ohm's law was used:

$$Q = EIt$$

where:
$Q$ = electrical heat input (in calories)
$I$ = amperes
$E$ = volts
$t$ = time (in seconds)

Substituting the numbers obtained in the electrical calibration:

$$Q = 0.50383 \times 10.3861 \times 2280 = 11931 \text{ (joules)}$$

Using the conversion factor 1 calorie = 4.1840 joules, the final figure becomes:

$$\frac{11931}{4.1840} = 2851.6 \text{ calories}$$

The energy equivalent was then determined from the equation:

$$\Sigma_c = \frac{Q}{\Delta T_e}$$

where:
$E_c$ = energy equivalent (in calories/degree)
$Q$ = electrical heat input
$\Delta T_e$ = temperature change from electrical energy Substituting the numbers obtained in the electrical calibration:

$$\Sigma_c = \frac{2851.6}{5.840} = 488.3 \text{ calories/degree}$$

The energy equivalent figure was then used to calculate the heat of reaction derived in forming the sulfonate product. The equation is:

$$Q_r = E_c \Delta T_c$$

where:
$Q_r$ = heat of reaction (in calories)
$E_c$ = energy equivalent
$\Delta T_c$ = temperature change from chemical energy Substituting the figures obtained in the reaction step and the calibration step:

$$Q_r = 488.3 \times 4.83 = -2358.5 \text{ calories}$$

The figure above is the heat term value for the experiment. This figure is given a negative sign to indicate that the experiment is an exothermic reaction. The heat term value is converted to kilocalories/mole according to the following equation:

$$\Delta H_r = \frac{Q_r}{m}$$

where:
$\Delta H_r$ = molar heat of reaction (in kilocalories/mole)
$m$ = gram moles of sulfonate produced in the reaction Substituting in the equation, therefore:

$$\Delta H_r = \frac{-2358.5}{0.1860}$$

$$= -12,681 \text{ calories/mole}$$
$$= -12.68 \text{ kilocalories/mole}$$

The invention claimed is:

1. A method for measuring the energy of a chemical reaction in an adiabatic calorimeter apparatus, the calorimeter apparatus including a reaction chamber defined by a spherical cavity enclosed by an insulated box structure, the reaction chamber being filled with a gas atmosphere, the method comprising the steps of:

placing a first chemical reactant in an auxiliary vessel located in the spherical cavity;

placing a second chemical reactant in a reaction vessel located in the geometric center of the spherical cavity;

heating the auxiliary vessel, the reaction vessel, and the gas atmosphere to a predetermined initial temperature;

transferring the first chemical reactant from the auxiliary vessel to the reaction vessel to initiate a chemical reaction in the reaction vessel;

continuously stirring the reactants in the reaction vessel;

sensing any temperature difference between the gas atmosphere and the reaction vessel, as the reactants in the reaction vessel are undergoing a temperature change from the initial temperature;

continuously maintaining the temperature of the gas atmosphere in equilibrium with the temperature of the reaction vessel until the chemical reaction taking place in the reaction vessel is completed;

measuring the temperature change which the reactants in the reaction vessel are undergoing during the chemical reaction; and recording the temperature change of the reactants in the reaction vessel with a temperature recorder unit.

2. The method of claim 1 which includes the step of continuously circulating the gas in the reaction chamber in a symmetrical pattern.

3. The method of claim 1 which includes the step of measuring the amount of pressure generated by the chemical reaction taking place in the reaction vessel.

4. An adiabatic calorimeter apparatus for measuring the energy of a chemical reaction, the apparatus comprising:

a reaction chamber defined by a cavity (13) positioned within an insulated box structure (10);

the reaction chamber being filled with a gas atmosphere;

a closed auxiliary vessel (15) which is positioned in the reaction chamber, the auxiliary vessel (15) containing a first chemical reactant;

a source of gas under pressure, the gas source being in communication with the auxiliary vessel (15);

a closed reaction vessel (55) which is positioned in the reaction chamber, the reaction vessel (55) containing a second chemical reactant;

a transfer conduit (69) which connects the auxiliary vessel (15) to the reaction vessel (55), for carrying the first chemical reactant from the auxiliary vessel (15) into the reaction vessel (55) upon applying the gas under pressure to the auxiliary vessel (15);

a first heater means (64) which is positioned in the reaction vessel (55), and is connected into a first electrical power supply;

a temperature measuring means (63) positioned in the reaction vessel (55);

a temperature recorder unit (34) which is connected into the temperature measuring means (63), for continuously recording the temperature in the reaction vessel (55);

a first differential temperature sensing system which comprises a first temperature sensing means (37), a second temperature sensing means (39), a second heater means (35), a first temperature control unit (28), and a second electrical power supply;

the first temperature sensing means (37) being attached to the reaction vessel (55); the second temperature sensing means (39) and the second heater means (35) being attached to an inner wall surface of the reaction chamber, the first and second temperature sensing means (37, 39) being connected together, and the first temperature control unit (28) being connected into the first and second temperature sensing means (37, 39), the second heater means (35), and the second electrical power supply;

the first temperature control unit (28) thereby sensing any temperature differential between the reaction vessel (55) and the gas atmosphere, and adjusting the differential to maintain the temperature of the reaction vessel (55) and the gas atmosphere at equilibrium; and a second differential temperature sensing system which comprises a third temperature sensing means (48), a fourth temperature sensing means (47), a third heater means (43), a second temperature control unit (46), and a third electrical power supply;

the third temperature sensing means (48) being attached to the reaction vessel (55), the fourth temperature sensing means (47) and the third heater means (43) being attached to the auxiliary vessel (15), the third and fourth temperature sensing means (48, 47) being connected together, the second temperature control unit (46) being connected into the second and third temperature sensing means (48, 47), the third heater means (43), and the third electrical power supply;

the second temperature control unit (46) thereby sensing any temperature differential between the reaction vessel (55) and the auxiliary vessel (15) and adjusting the differential to thereby maintain the temperature of both vessels at equilibrium.

5. The calorimeter apparatus of claim 4 in which the reaction chamber is a spherical cavity (13), the cavity (13) is enclosed by the insulated box structure (10), the reaction vessel is suspended in the geometric center of the cavity (13) by a suspension means (16), and the suspension means is attached to the reaction vessel (55) and to a wall surface (19) defined by the periphery of the cavity (13).

6. The calorimeter apparatus of claim 4 in which the insulated box structure (10) is fabricated of a plastic foam or a ceramic foam.

7. The calorimeter apparatus of claim 4 in which the first heater means is a resistance wire heater (64), said heater is positioned in a first well member (56), and the first well member (56) is positioned inside the reaction vessel (55).

8. The calorimeter apparatus of claim 4 in which the temperature measuring means is a resistance thermometer (63), said thermometer is positioned in a second well member (57), and the second well member (57) is positioned inside the reaction vessel (55).

9. The calorimeter apparatus of claim 4 in which the first temperature sensing means is a group of thermocouples (37), the second temperature sensing means is a group of thermocouples (39), and the second heater means is a group of resistance heaters (35).

10. The calorimeter apparatus of claim 4 in which the third temperature sensing means is a group of thermocouples (48), the fourth temperature sensing means is a group of thermocouples (47), and the third heater means is a sleeve heater (43).

11. The calorimeter apparatus of claim 4 which includes a stirring means, said stirring means comprising a metal stir bar (23), and a magnet (24), the magnet (24) being attached to a rotatable shaft (25), the stir bar being positioned in the reaction vessel (55), and the rotatable shaft extending into the cavity (13) such that the magnet is positioned adjacent to the reaction vessel (55).

* * * * *